United States Patent [19]
Fuller

[11] Patent Number: 5,554,359
[45] Date of Patent: Sep. 10, 1996

[54] PIGMENTATION ENHANCER AND METHOD

[75] Inventor: Bryan B. Fuller, Edmond, Okla.

[73] Assignee: The Board of Regents of the University of Oklahoma, Norman, Okla.

[21] Appl. No.: 251,072

[22] Filed: May 31, 1994

Related U.S. Application Data

[63] Continuation-in-part of Ser. No. 943,998, Sep. 11, 1992, abandoned, which is a continuation of Ser. No. 451,420, Dec. 15, 1989, abandoned.

[51] Int. Cl.$^6$ ................................ A61K 7/42; A61K 7/40
[52] U.S. Cl. ................................ 424/59; 424/60; 424/63
[58] Field of Search ................................ 424/59, 63, 60

[56] References Cited

U.S. PATENT DOCUMENTS

| | | | |
|---|---|---|---|
| 3,937,809 | 2/1976 | Jacobi | 424/60 |
| 4,515,773 | 5/1985 | Herlihy | 424/59 |
| 4,707,354 | 11/1987 | Garlen et al. | 424/47 |
| 4,956,489 | 9/1990 | Auriol et al. | 560/40 |
| 4,968,497 | 11/1990 | Wolfram et al. | 424/59 |
| 5,273,550 | 12/1993 | Prota | 8/405 |
| 5,279,617 | 1/1994 | Prota et al. | 8/406 |
| 5,279,618 | 1/1994 | Prota et al. | 8/406 |

OTHER PUBLICATIONS

H. Saeki and A. Oikawa, "Stimulation of Tyrosinase Activity of Cultured Melanoma Cells by Lysosomotropic Agents", *Journal of Cellular Physiology*, 1983, 116:93–97.

M. Pathak, "Activation of the Melanocyte System by Ultraviolet Radiation and Cell Transformation", *Annals New York Academy of Sciences*, 1985, 453:328–339.

H. Saeki and A. Oikawa, "Stimulation by Ionophores of Tyrosinase Activity of Mouse Melanoma Cells in Culture", *The Journal of Investigative Dermatology*, 1985, 85:423–425.

Abstract of HCAPLUS, vol. 108:107130, [Abstract of WO 8704623 (Aug. 13, 1987)] Hruby et al.

Medline Abstract of J. of Cell Immunol, vol. 113(2), pp. 387–403, May 1988.

Biosis Abstract of Invest New Drugs vol. 6(4), 1988, pp. 251–258, Dorr et al.

HCAPLUS Abstract of WO9006104, Meybeck et al.

Medline Abstract of J. Biol. Chem, Mar. 15, 1986, Harper et al.

Medline Abstract of J. of Pigment Cell Res. 1987, pp. 44–50, Oikawa et al.

Biosis Abstract of J. Invest. Dermatology, vol. 89, 1987, pp. 269–273, Levine et al.

Biosis Abstract of Life Science, vol. 40(19), 1987 pp. 1889–1896, Hadley et al.

Derwent Abstract of Germany patent No. DE2,932,923, Feb. 19, 1981, Mausner.

Derwent Abstract of German patent No. DE3229738, Feb. 16, 1984, Cao et al.

Derwent Abstract of WO9107167, Sep. 28, 1993, Schering–Plough.

Derwent Abstract of Japanese patent No. 04182492, Jun. 30, 1992, Kao Corp.

*Primary Examiner*—Shelley A. Dodson
*Attorney, Agent, or Firm*—Dunlap & Codding, P.C.

[57] ABSTRACT

A composition comprising a lysosomotropic agent, and optionally phosphodiesterase inhibitors, and/or methylxanthines for increasing synthesis of melanin in a human melanocyte thereby enhancing pigmentation of the human skin. Use of this composition promotes tanning of the human skin and increases photoprotection from ultraviolet radiation. An organ culture system comprising viable human foreskin samples which may be used to test the effects of agents on human skin, including pigmentation enhancers on human skin.

27 Claims, 7 Drawing Sheets

PIGMENTATION ENHANCER AND METHOD

The present application is a continuation-in-part of Ser. No. 07/943,998, filed Sep. 11, 1992, now abandoned, which is a continuation of Ser. No. 07/451,420, filed Dec. 15, 1989, now abandoned.

FIELD OF THE INVENTION

The present invention generally relates to compositions for topical application on a subject's skin, and specifically, to pigmentation enhancers, and to methods for assaying the effects of compositions on skin.

SUMMARY OF THE INVENTION

The present invention comprises a composition of matter comprising an amount of a lysosomotropic agent effective in increasing levels of melanin in a human melanocyte. The composition also comprises an effective amount of a pharmaceutically acceptable topical carrier. The carrier is capable of delivering the lysosomotropic agent to the melanocyte under in vivo conditions.

The composition of matter of the present invention may further comprise an amount of a methylxanthine and/or a phosphodiesterase inhibitor which is effective in increasing levels of melanin in a human melanocyte. The composition also comprises an effective amount of a pharmaceutically acceptable topical carrier capable of delivering the methylxanthine and/or phosphodiesterase inhibitor to the melanocyte under in vivo conditions. The carrier for delivering the methylxanthine or phosphodiesterase inhibitor may be the same carrier for delivering the lysosomotropic agent.

The present invention also comprises a method for at least partially shielding the skin from ultraviolet radiation in a subject. The subject's skin is treated with a pigment enhancer comprising a lysosomotropic agent and optionally a methylxanthine and/or phosphodiesterase inhibitor effective in increasing the amount of melanin in a human melanocyte, and a pharmaceutically acceptable topical carrier as previously described.

Another method of the present invention is a method of promoting tanning of a subject's skin. The skin is treated topically with a pigment enhancer as described above.

The present invention is also directed to a human organ culture comprising a viable human foreskin tissue specimen having an epidermis and a dermis, a nutrient medium, and a means for supporting the foreskin in the medium. The foreskin is supported such that the dermis contacts the medium, and the epidermis is in substantially non-contacting relationship with the medium.

The human organ culture may be used to assay the effects of agents on skin. A baseline level of a biological factor in the foreskin is observed. The foreskin is contacted with the agent, and a post-contact observation made of the biological factor in the foreskin.

DETAILED DESCRIPTION OF THE PREFERRED EMBODIMENTS

Skin color in humans arises from a complex series of cellular processes which are carried out within a unique population of cells called melanocytes. Melanocytes are located in the lower part of the epidermis, and their function is to synthesize a brown pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the cell. The melanosomes are extruded from the cell and carried to the surface of the skin by keratinocytes, which internalize the melanin containing melanosomes. The end result is that the visible layers of the skin exhibit a brown color typically known as a "tan".

The darkness of the color observed in the skin is proportionate to the amount of melanin synthesized by melanocytes and transferred to the keratinocytes. By increasing melanogenesis, skin can be at least partially shielded from ultraviolet radiation, and tanning of the skin can be achieved without exposure of the skin to potentially damaging ultraviolet radiation. The present invention is directed to compositions and methods which increase melanogenesis in subjects. "Subjects" as used herein mean mammals, and, more preferably, humans.

The present invention comprises compositions comprising an effective amount of one or more agents capable of increasing the amount of melanin in a melanocyte (hereafter "melanin-increasing agent") and, more preferably, in a human melanocyte, and more preferably, in melanocytes in intact human skin. The melanin-increasing agent may function in any of the various ways that are believed to increase the amount of melanin: by increasing cAMP (cyclic AMP) or derivatives of cAMP which function as cAMP in the melanocyte; by inhibiting phosphodiesterase; or by increasing tyrosinase activity. The melanin-increasing agent should be capable, alone or with the aid of a carrier as described hereafter, of crossing the melanocyte membrane, and more preferably, a human melanocyte membrane, in order to function as will be described.

Preferably, the melanin-increasing agent of the present invention comprises at least one lysosomotropic agent and, optionally a phosphodiesterase-inhibitor and/or methylxanthine. Phosphodiesterase-inhibitors are believed to increase the amount of cAMP in biological systems. Cyclic-AMP is believed to increase the activity of tyrosinase, which is the rate limiting enzyme which transforms the substrate tyrosine into melanin.

The melanin-increasing agent of the present invention comprises at least one lysosomotropic agent, and optionally a methylxanthine which is preferably a methylxanthine capable of functioning as a phosphodiesterase inhibitor. Most preferably, the additional agent comprises theophylline, isobutyl methylxanthine (IBMX), or a derivative thereof such as aminophylline. Additionally, melanin-increasing agents of the present invention may be combined in order to enhance pigmentation of the individual.

The melanin-increasing agent may also comprise any pharmaceutically acceptable salt, analog, derivative or isomer of any phosphodiesterase inhibitor, or methylxanthine or lysosomotropic agent capable of functioning as described herein.

A lysosomotropic compound is defined herein as a compound which enters a cell, accumulates in lysosomes, and causes a decrease in the lysosome transmembrane proton gradient, thereby increasing the pH inside the organelle. Lysomotropic agents are known to increase the internal pH of acidic vesicles and include the compounds ammonium chloride, monensin, nigericin, methylamine and ethylamine. The addition of such compounds may activate preexisting but catalytically inactive tyrosinase in melanosomes.

Preferably, the melanin-increasing agent is present in the composition in a concentration of from about 0.01 mM to about 100 mM. In a preferred embodiment, 18 mg of theophylline may be combined with 10 ml of a pharmaceutically acceptable topical carrier to cover about a 50 square inch area of skin. In another preferred embodiment, 180 mg of theophylline may be combined with 10 ml of a pharmaceutically acceptable topical carrier to form a composition capable of covering about a 50 square inch area of skin. In another embodiment, 2.2 mg of isobutyl methylxanthine may be combined with 10 ml of a pharmaceutically acceptable carrier to cover about a 50 square inch area of skin.

As previously discussed, the enzyme tyrosinase converts the substrate tyrosine into melanin. Since the composition of the present invention is believed to increase tyrosinase activity, the present invention optionally further comprises an effective amount of tyrosine so that the tyrosinase has as much substrate as possible to synthesize melanin. An "effective amount" of tyrosine means any amount which can be utilized by tyrosinase over the amount of tyrosine already present in the melanocyte. A preferable amount of tyrosine is about 0.01 mM to about 1 mM of the composition of the present invention. In a preferred embodiment, 1.8 mg of tyrosine may be combined with 18 mg of theophylline and 10 ml of a pharmaceutically acceptable topical carrier.

The composition of matter of the present invention is preferably applied directly to the skin of the individual seeking tanning of the skin and/or photoprotection from ultraviolet radiation. The treated area can be the entire skin surface of the subject or only those areas normally exposed to ultraviolet radiation. Since the composition of the present invention does not dye the skin, but rather permits the body chemistry to produce the tan, the tanning will not be streaked in the areas of application. Application of the composition may be repeated periodically for greater protection and/or tanning effect.

The composition of matter is preferably in a lotion or solution form which may be manually rubbed on the skin. Other means of application are acceptable such as aerosol sprays or the use of an applicator bottle.

ORGAN CULTURE SYSTEM

The adequate evaluation of the effects of an agent applied to human skin has been difficult, if not impossible, due to the nature of the systems previously used. For example, to study the pigmentation process, mouse melanoma cells, human melanoma cells, and human melanocytes in culture treated with tumor promotor agents have been used. The results of experiments using these abnormal cells were often inconsistent and did not always correlate to the results obtained in the normal human skin.

Rather than use abnormal cells placed outside their normal environment, the present invention comprises cells in situ in an organ and maintains the viability of the organ in order to emulate the human skin in vivo. It is the development of a human organ culture system of the present invention which has permitted the adequate evaluation and development of the compositions and methods of treatment of the present invention.

The human organ culture of the present invention employs a viable foreskin. "Viable" means there has been no substantial morphological change in the foreskin after surgical removal. Viability may be determined by changes in tissue ultrastructure determined through histochemical staining and/or dopa reaction staining, techniques which permit monitoring of any changes in the tissue ultrastructure.

The foreskins may be obtained by circumcising male neonates by standard surgical procedures. After surgical removal, the foreskin is preferably prepared for the organ culture by injection intradermally with the medium described hereafter. This swells the mucous membrane and allows for the removal of the membrane thereby allowing adequate nutrient flow to the foreskin through the dermis.

The foreskin comprises an epidermis which is normally exposed to the environment and a dermis opposing the epidermis. After surgical removal and preparation for the organ culture, the dermis, which is normally supplied nutrients by the body, is exposed to the environment. In order to maintain the viability of the foreskin, a nutrient medium supplies nutrients to the foreskin through the dermis as described hereafter.

The nutrient medium is any composition which maintains the viability of the foreskin. Preferably, the nutrient medium has a liquid phase such as a solution, suspension or emulsion. A portion of the medium may be obtained commercially, such as Iscove's modified Dulbecco's medium (IMDM), Ham's nutrient mixture F-10 medium, Minimum essential media (MEM), RPMI media 1630 or 1640, Dulbecco's Modified Eagle Media (D-MEM) or Media 199 all of which are manufactured by Gibco Laboratories of Grand Island, N.Y. as well as other companies, the specification sheets of which are hereby incorporated by reference. Additionally the medium comprises about 10% to about 30% horse serum and about 2% to about 10% fetal bovine serum; the serums may be purchased from Hyclone Lab Inc., of Logan, Utah. If necessary, an alkalizer such as sodium bicarbonate may be added until the medium achieves a preferred pH, preferably about a physiological pH. Antibiotics such as penicillin and/or streptomycin may also be added for microbial control.

If transportation of the foreskin is necessary after surgical removal, the foreskin is immediately placed on an absorbent support saturated with the nutrient medium. In order to maintain the viability of the foreskin, the foreskin is disposed in the medium within about 3–4 hours after surgical removal. The position of the foreskin in the medium should be that the dermis contacts the medium and the epidermis is not substantially contacted by the medium.

Figure 1:
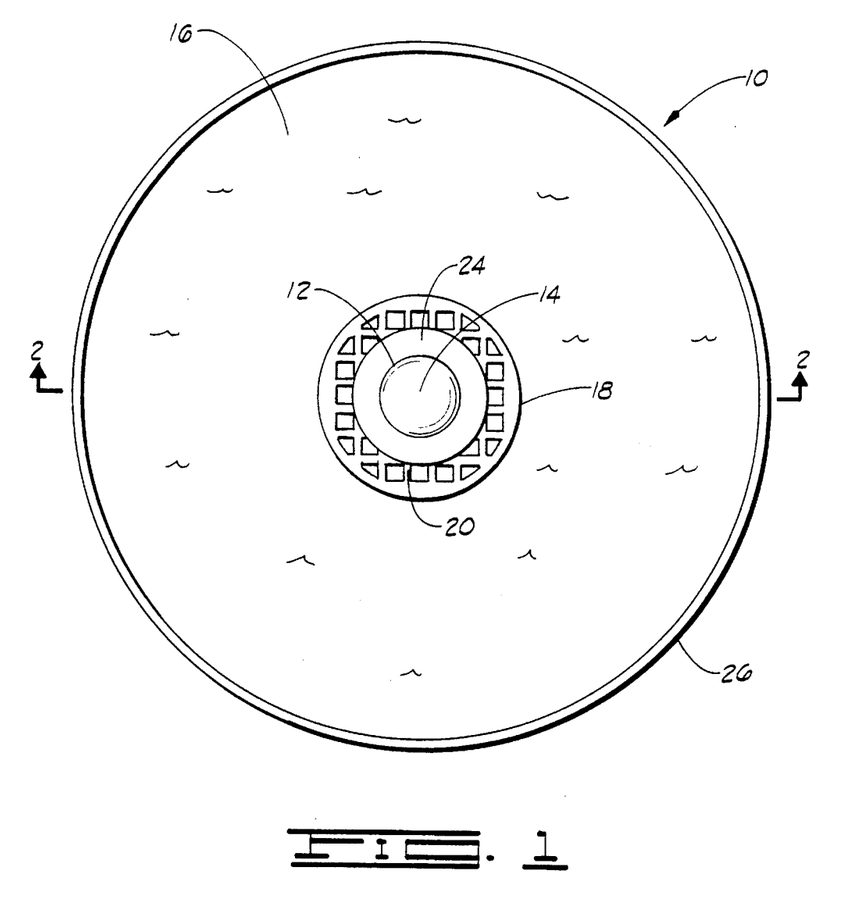
FIG. 1 is a plan view of the organ culture system of the present invention.
Figure 2:
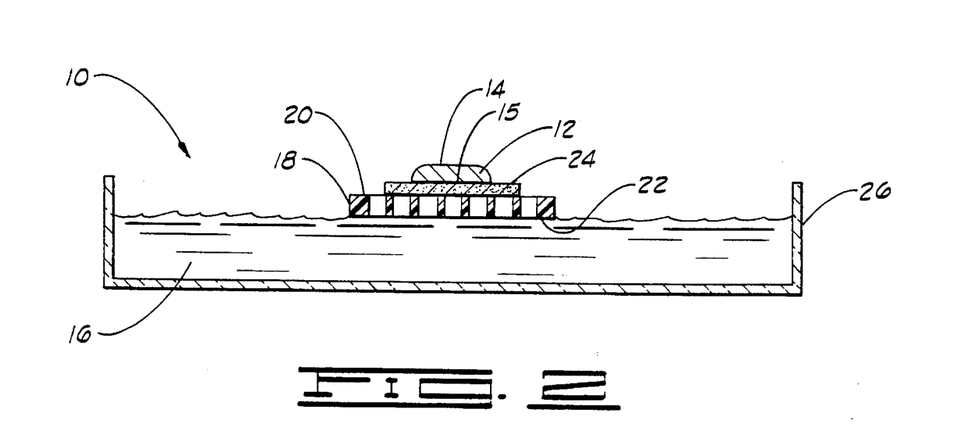
FIG. 2 is a side cross-section view of the organ culture system shown in FIG. 1 taken along line 2—2 shown in FIG. 1.

Referring to FIGS. 1 and 2 of the organ culture system 10, the present invention comprises a foreskin 12, having an epidermis 14 and a dermis 15. The foreskin 12 is placed in the medium 16 so that the medium 16 contacts the dermis 15 but does not substantially contact the epidermis 14. The epidermis 14 is in contact with the environment as under in vivo conditions. The medium 16 nourishes the foreskin 12, and maintains its viability while the organ culture is under study. About 7 days or less are generally needed to complete such a study.

The medium 16 comprises a liquid phase and is disposed in a container such as a petri dish 26. The amount of medium needed will depend upon, among other things, the container and the support means used. Generally about 5 ml to about 10 ml is a sufficient amount of medium for one foreskin in a petri dish having a diameter of 1.5 inches with the foreskin supported on a float as described hereafter.

The foreskin 12 may be supported by any means which will permit positioning of the foreskin in the medium 16 as previously described. Preferably, the foreskin 12 is disposed on a buoyant and permeable float 18 having a top 20 and a bottom 22; the dermis 15 contacts the top 20 of the float 18. The float 18 floats on top of the medium 16. The float 18 preferably comprises a sterile plastic screen such as a Swinnex 25 cm filter support screen manufactured by Millipore. More preferably, a permeable pad 24 is interposed between the dermis 15 and the top 20 of the float 18. The pad 24 functions to hold the foreskin 12 on the float 18. One example of a pad 24 used in accordance with the present invention is a AP20 025 00 filter manufactured by Millipore. Because both the float 18 and pad 24 are permeable to the culture medium 16, the medium maintains contact with the dermis 15 while the foreskin is positioned on the float 18, as required to maintain the foreskins viability. The float 18 is placed on top of the medium 16 and may freely move about the top of the medium 16.

Once the foreskin is disposed in the organ culture system as described herein, the organ culture system is incubated during the length of observation of the foreskin. Preferably the medium is changed daily, since nutrients may be depleted over time, and the incubation causes degradation of medium components.

In using the human organ culture system of the present invention, the foreskin is surgically removed, prepared and disposed in the organ culture system as described herein. Before positioning the foreskin in the system, the foreskin should be observed to determine the amount and/or the condition of the biological factor under study to obtain a baseline measurement.

After treatment of the foreskin with an agent, the biological factor is again observed for a post-treatment measurement to be compared to the baseline measurement. For example, if the amount of tyrosinase in the foreskin is under study, the amount of tyrosinase is determined as a baseline measurement prior to application of the agent to the foreskin. If the toxicity of an agent on skin is to be studied, the foreskin may be observed for DNA synthesis, protein synthesis, ATP synthesis, or any combination of these cell functions. If the permeability of an agent on skin is to be determined, the absence of the agent in the skin is the baseline measurement. Some examples of biological factors which may be studied are tyrosinase, melanin, DNA, RNA, proteins, carbohydrates, or any other factor that can be measured or observed for differences between the treated and the untreated foreskins.

If the foreskin is to be treated with an agent under study, the agent should be added to the medium 16, so that it comes into contact with the foreskin 12 through the medium 16. Alternatively, the agent can be placed directly on the epidermis 14. The treatment time will depend on the results sought, the identity of the agent under study, the time over which the foreskin can remain viable, and other variables.

After the foreskin has been treated with the agent under study, the foreskin may be observed and/or tested in any manner which will determine the differences in the foreskin from the observation and/or tests on the untreated foreskin. For example, the activity of tyrosinase may be measured as described herein and correlated to an increase in melanogenesis; the rate of DNA synthesis can be measured by $^3$H-thymidine uptake and compared to controls; or the increase or decrease in the synthesis of proteins and/or RNA can be measured by determining the rate of incorporation of [$^3$H] leucine (protein) or [$^3$H] uridine (RNA) into acid-precipitating material.

From the foregoing, it will be appreciated that the organ culture system of the present invention offers an opportunity to study the effects of many agents on human skin, and many biochemical processes of human skin. Factors other than pigmentation processes, and agents other than pigmentation enhancers may be evaluated for effects on the skin. For example, cosmetic agents or suspected toxic environmental compounds may be tested for their effects on skin morphology, DNA synthesis, abnormal chromosome appearance, skin cell viability, and protein and RNA synthesis. Also, the permeability of agents through the epidermis and the dermis may be studied in order to evaluate agents for use in transdermal delivery systems for systemic delivery of the agent.

The following examples illustrate the practice of the method and composition of the present invention:

EXAMPLE 1

Preparation of Human Foreskin

At the time of surgical removal, human foreskins were placed on sterile gauze saturated with sterile IMDM medium (Iscove's modified Dulbecco's medium purchased from Irvine Scientific of Santa Ana, Calif.) for transportation from the Hospital nursery to the laboratory. The tissues were rinsed in sterile IMDM medium containing 500 U/ml penicillin and 500 µg/ml of streptomycin for 5 minutes. Under sterile conditions, an intradermal injection of medium was performed from the dermal side prior to dissection of the mucous membrane and lower dermis by scissors to make the thickness of skins equal. The foreskins were then cut into approximately 3 mm×3 mm squares and either frozen at −75° C. or placed in organ culture as described hereafter.

EXAMPLE 2

Organ Culture

The organ culture medium was prepared from IMDM with glutamine supplemented with 20% horse serum, 5% fetal bovine serum, 100 U/ml penicillin, 100 µg/ml streptomycin and 3 mg/ml sodium bicarbonate. The serums were obtained from Hyclone Lab. Inc. of Logan Utah. Culture units were prepared by placing sterilized filters (AP20 025 00, Millipore) over sterilized support screens (25 cm Swinnex filter support screens, Millipore) in the wells of 6-well tissue culture plates (Falcon 3046) with medium added to the wells such that the skin support screens floated and the filter absorbed the medium from beneath. The tissue samples were placed, epidermis up, on top of the saturated filters and incubated at 37° C. in a 5% $CO_2$ humidified atmosphere. The medium was changed everyday. Harvested cultures were frozen at −75° C.

EXAMPLE 3

Light Microscopy

For histological study, thawed samples of fresh tissue and explants were mounted in OCT compound (ICN Immuno Biologicals, Lisle, Ill.) and frozen by liquid nitrogen. Cryostat sections (6 μm thick) were fixed in 2% formaldehyde for 2 hours at 40° C., and then stained either with hematoxylin and eosin or subjected to dopa staining. The dopa reactions were carried out by incubation in two changes of 0.1% L-dopa solution buffered to pH 7.4 in 0.1M sodium phosphate buffer for 4 hours at 37° C.

EXAMPLE 4

Determination of Tyrosinase Activity

Tyrosinase activity in human skin organ cultures was determined by measuring the tyrosine hydroxylase activity of the enzyme. The assay measures the production of $^3H_2O$ during the conversion of [$^3H$]tyrosine to L-DOPA. Weighed skin preparations were incubated in 0.3 ml of a reaction mixture containing 0.01 mM of L-tyrosine, 5–6 uCi/ml of [$^3H$]tyrosine and 0.1 mM L-DOPA in 0.1M of pH 6.8 phosphate buffer for 4 hours at 37° C. To terminate the reaction, 1 ml of phosphate buffer was added, the tubes vortexed, and 0.4 ml aliquots removed in triplicate and mixed with an equal volume of Norit SG activated charcoal (10% w/v, in 0.1N HCl). Following centrifugation at 2000×g for 10 min, the supernatants (0.5 ml) were placed in scintillation vials, scintillation fluid added, and vials counted in a TM Analytic 6895 scintillation counter equipped with a DPM processor.

EXAMPLE 5

Evaluation of Viability of the Human Foreskin

In order to assess the efficacy of the culture system, both black and white human foreskins were placed in culture and at 24 hours intervals skin sections were removed for histological examination by H&E staining and by dopa staining. The human foreskin retained its normal morphology throughout the 7 day length of the study. There was no difference in structural viability between black and white skin. When the dopa oxidase activity of cultured skin melanocytes was examined by dopa staining, a similar staining pattern between day 0 and day 7 foreskin cultures was observed, showing that the culture conditions maintain the viability of the skin for many days. Foreskins placed in culture within 3–4 hours of surgical removal showed normal structural integrity throughout the culture period whereas samples placed in culture more than 4 hours after removal did not maintain structural integrity.

When tyrosinase activity levels were determined in cultured skin, a marked decline in activity during the first 24 hours in culture in both black and white foreskins was observed. After this initial drop, however, tyrosinase activity stabilized for the remainder of the 7 day incubation period.

EXAMPLE 6

Evaluation of Foreskin Treatment

Foreskins treated with α-MSH (melanocyte stimulating hormone from Sigma, St. Louis, Mo.) showed an increase in tyrosinase activity whereas foreskins treated with D-phe-MSH (Sigma, St. Louis, Mo.) showed a marked stimulation of tyrosinase. This shows that the organ culture system can respond to hormones. A stronger stimulation of tyrosinase was found with theophylline. Human foreskins were treated with the compounds shown in Table 1, placed in culture, and incubated for 72 hours. The skins were then assayed for tyrosinase activity with the tyrosine hydroxylase assay method as described herein. As shown in Table 1, dibutyryl cAMP was less effective in stimulating tyrosinase activity.

Table 2 shows the activity of theophylline in a pharmaceutical topical carrier. Organ cultures were incubated with the compounds shown in Table 2 for 72 hours. The medium and compounds were changed daily. Tyrosinase activity was determined by measuring the tyrosine hydroxylase activity of the enzyme.

Human foreskin organ cultures were treated with the compounds listed in Table 3 for 3 days and tyrosinase activity determined as described herein. Theophylline was used at 1 mM.

TABLE 1

Summary of effects of hormones and other compounds on tyrosinase activity in human foreskin organ cultures.

| | Tyrosinase Activity | |
|---|---|---|
| Treatment | Stimulated | Unaffected |
| Theophylline (1 mM) | 11B(92%); 6W(86%) | 1B(8%); 1W(14%) |
| MSH (2 × 10$^{-7}$ M) | 2B(33%); 2W(40%) | 4B(67%); 3W(60%) |
| dbcAMP (0.1 mM)[a] 6B(67%); 3W(75%) | 3B(33%); 1W(25%) | |
| D-phe-MSH(10$^{-8}$ M) | 2B(50%); 2W(50%) | 2B(50%); 2W(50%) |

[a]dbcAMP is dibutyryl cAMP. B = black; W = white;.
Values are the averages of triplicate determinations ± s.d.

TABLE 2

Effect of IBMX (isobutyl methylxanthine) and theophylline in vehicle[a] on tyrosinase activity in human foreskin organ cultures.

| Treatment | Tyrosinase Activity pmoles $^3H_2O$/hour/mg skin |
|---|---|
| control | 3.15 ± 0.1 |
| IBMX (0.1 mM) | 7.03 ± 0.49 |
| Theophylline/ vehicle (1 mM) | 6.32 ± 0.22 |

[a]vehicle consists of 20% water, 50% isopropanol and 30% glycerol.
Values are the average of triplicate assays ± s.d.

TABLE 3

Effect of Hormones and other compounds on tyrosinase activity in human foreskin organ cultures.

| Skin Type | Treatment | Tyrosinase Activity pmoles $^3H_2O$/hr/mg skin | Percentage of control |
|---|---|---|---|
| Black | control | 2.55 ± 0.13 | |
| | theophylline | 5.40 ± 0.26 | 212 |
| Black | control | 3.09 ± 0.12 | |

TABLE 3-continued

Effect of Hormones and other compounds on tyrosinase activity in human foreskin organ cultures.

| Skin Type | Treatment | Tyrosinase Activity pmoles $^3$H$_2$O/hr/mg skin | Percentage of control |
|---|---|---|---|
| | theophylline | 6.1 ± 0.24 | 197 |
| White | control | 0.31 ± 0.03 | |
| | theophylline | 0.95 ± 0.05 | 307 |
| | D-phe-MSH ($10^{-9}$ M) | 0.51 ± 0.05 | 165 |
| Hispanic | control | 0.41 ± 0.02 | |
| | D-phe-MSH ($10^{-8}$ M) | 1.43 ± 0.16 | 349 |
| | D-phe-MSH ($10^{-9}$ M) | 0.91 ± 0.03 | 222 |

Values are the averages of triplicate determinations ± s.d.

Stimulation of Melanogenesis by Lysosomotropic Agents

The present invention is a composition for use in stimulating melanogenesis in human skin cells, and a method for using such a composition for promoting melanogenesis and tanning in intact human skin. The composition comprises an amount of a lysosomotropic agent effective in increasing levels of melanin in a human melanocyte, and an effective amount of a pharmaceutically acceptable topical carrier capable of delivering the lysosomotropic agent to the melanocyte under in vivo conditions. The lysosomotropic agent of the composition may be selected from the group consisting of ammonium chloride, monensin and nigericin, or any other lysosomotropic agent which functions in accordance with the invention as defined herein. The lysosomotropic agent may comprise a concentration in the composition of from about 0.1 mM to about 100 mM. The lysosomotropic agent also may comprise from about 0.01 percent to about 10 percent by weight of the composition. More preferably, the lysosomotropic agent may comprise from about 0.02 percent to about 5 percent by weight of the composition. Even more preferably, the lysosomotropic agent may comprise from about 0.02 percent to about 2 percent by weight of the composition. The composition may further comprise an effective amount of dibutyryl cAMP.

In another version of the invention, the composition may comprise, in addition to the lysosomotropic agent, a methylxanthine and/or a phosphodiesterase inhibitor. The methylxanthine may be selected from the group consisting of theophylline, isobutyl methylxanthine, aminophylline and analogs, derivatives, isomers and pharmaceutically acceptable salts of theophylline, isobutyl methylxanthine or aminophylline which are capable of increasing melanin in the human melanocyte. In this composition, the lysosomotropic agent and the methylxanthine and/or phosphodiesterase inhibitor preferably comprise together from about 0.01 percent to about 10 percent by weight of the composition of matter. When the composition comprises a methylxanthine, the composition also comprises a carrier effective in delivering the methylxanthine to the melanocyte under in vivo conditions. The carrier which delivers the lysosomotropic agent and the methylxanthine and/or phosphodiesterase inhibitor may be the same.

Any of the compositions described herein may be used in a method for stimulating melanogenesis in human skin cells. Said method comprises (1) providing an effective amount of a composition comprising an effective amount of a lysosomotropic agent capable of increasing levels of melanin in a human melanocyte, and an effective amount of a pharmaceutically acceptable topical carrier capable of delivering the lysosomotropic agent to the melanocyte under in vivo conditions, and (2) applying the effective amount of the composition topically to human skin. The lysosomotropic agent used may comprise one or more of the lysosomotropic agents described herein and may be used in combination with a methylxanthine and/or phosphodiesterase inhibitor as described elsewhere herein and further may comprise an effective amount of dibutyryl cAMP.

The mouse melanoma cell lines used to study the effects of lysosomotropic agents herein were the Cloudman S91 cell line (ATCC no. CCL 53.1) and two subclones of this line developed in our laboratory, the amelanotic line, AM-7, and a melanotic line, MEL-11A. All melanoma cell lines were grown in Ham's F-10 nutrient medium supplemented with 10% horse serum, penicillin (100 units/ml), and streptomycin (100 μg/ml). The normal human melanocyte cell strains used in this study were derived from foreskins of either neonares or from boys 2–6 years old. Human melanocyte cultures were grown in Ham's F-10 nutrient medium supplemented with 10% horse serum, 5% fetal bovine serum (FBS), 32 nM TPA (12-O-tetradecanoylphorbol 13-acetate), $10^{-4}$M IBMX(3-isobutyl-1-methylxanthine), penicillin (100 units/ml), and streptomycin (100 μg/ml).

To determine tyrosinase activity in situ in either melanoma cells or in human melanocyte cultures, the tyrosine hydroxylase activity of the enzyme was determined. Cells were seeded into 60-mm culture dishes at $2 \times 10^5$ cells/dish and allowed to attach overnight. The medium was then exchanged for the appropriate growth medium supplemented with 1 μCi/ml of [$^3$H]tyrosine (L-ring-3,5-$^3$H]-tyrosine, DuPont New England Nuclear), and with hormones, where indicated. Cells were grown in labeled medium for 24 hours, and at this time, the medium was removed and assayed for the presence of $^3$H$_2$O using the charcoal absorption method of Pomerantz. Tyrosinase activity in cell homogenates was determined by sonicating cell pellets in 0.1-M sodium phosphate buffer (pH 6.8) and then incubating 50-μl aliquots in 0.5 ml of a reaction mixture containing 0.1-mM tyrosine, 2 μCi/ml of [$^3$H]tyrosine, 0.1-mM L-DOPA (dihydroxyphenylalanine), and 0.1 mM PMSF (phenylmethylsulfonyl fluoride) at 37° C. for 2 hours. Reactions were terminated by the addition of 1 ml of charcoal (10% w/v in 0.1-N HCl). Samples were centrifuged, and the supernatants removed for determination of the amount of $^3$H$_2$O produced.

The amount of melanin in melanoma cells or in melanocytes was determined by incubating cell pellets in 2 ml of 1-N NaOH for 48 hours at 37° C. and then measuring the solubilized melanin at 400 nm.

To determine tyrosinase abundance in either mouse melanoma cells or in human melanocytes, cells (quantity of approximately $10^6$) were sonicated in 0.05-M sodium phosphate buffer (pH 6.8) containing 0.5% Triton X-100 and 0.1-mM PMSF incubated at 4° C. for 1 hour to release tyrosinase from melanosomal membranes, and then centrifuged at 50,000×g for 30 minutes at 4° C. The supernatants were mixed with sodium dodecylsulfate (SDS) sample treatment buffer (10% SDS and 10% glycerol in 0.5M Tris-HCl, pH 6.8 without betamercaptoethanol), and equal amounts of cell extract protein (25 μg protein; approximately $8 \times 10^4$ cells) were electrophoresed in duplicate on 10% SDS polyacrylamide gels. Following electrophoresis, the position of tyrosinase was determined by incubating the gel first in 0.5-M sodium phosphate buffer (pH 6.5) for 10 minutes, and then in 0.1% L-DOPA in 0.1-M sodium phosphate buffer (pH 6.8) at 37° C. Within 10 minutes a melanin band was clearly visible on the gel. The duplicate gel was electroblotted onto Immobilon P membranes (Millipore Corp.), and tyrosinase detected by immunoblotting using a rabbit antimouse tyrosinase antiserum, and an Immun-Lite™ chemiluminescent/alkaline phosphatase detection kit manufactured by Bio-Rad Laboratories (Richmond, Calif.). The chemiluminescent signal was detected by exposing the blot to Kodak XAR x-ray film for 15 minutes followed by development. Tyrosinase abundance was quantitated by determining the volume of the autoradiographic signal on a Molecular Dynamics model 300A computing densitometer.

Figure 3:
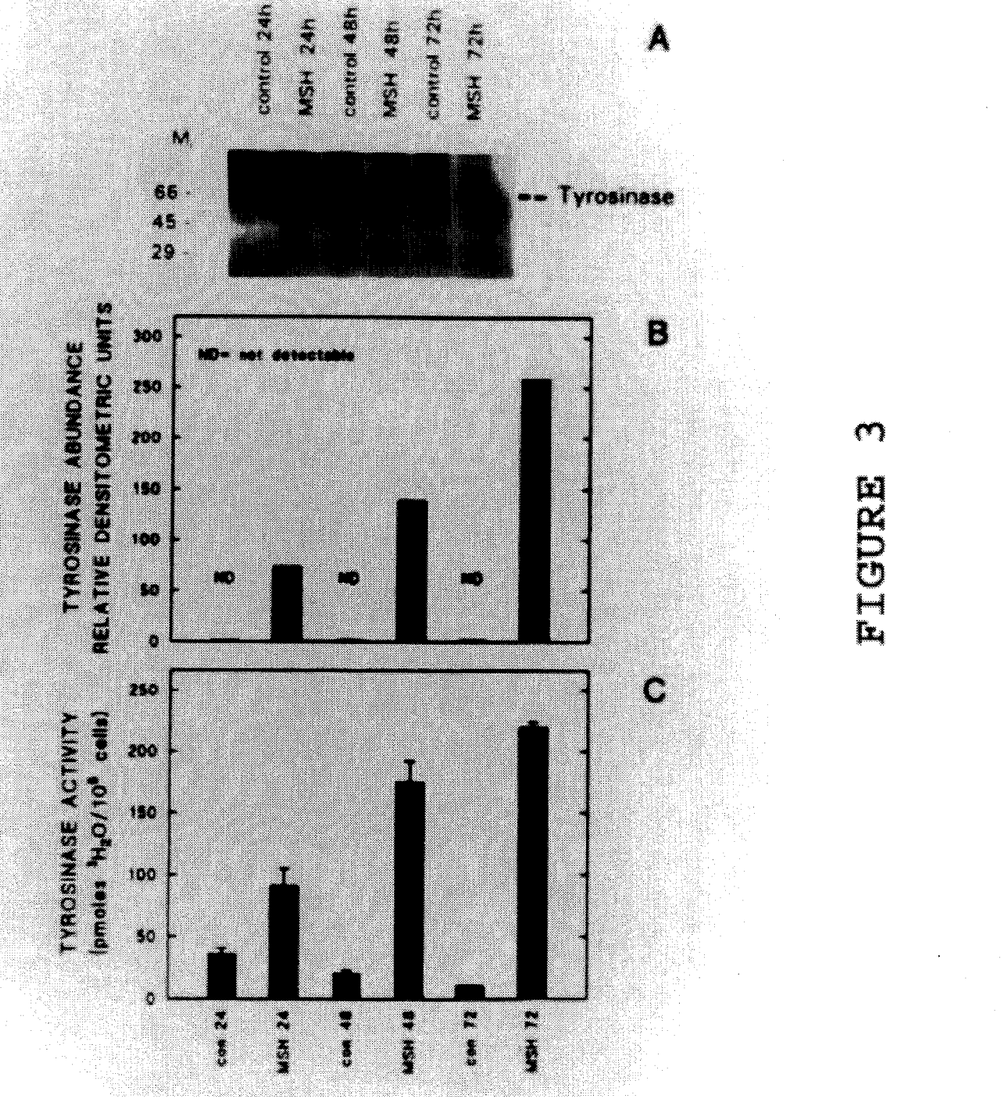
FIG. 3 shows the effects of melanocyte stimulating hormone on tyrosinase activity and abundance in mouse melanoma cells.

(FIG. 3: Cells were seeded in 75-$cm^2$ flasks at a density of $10^6$ cells/flask for the 24-hour experiment, at $5\times10^5$ cells/flask for the 48-hour time point, and at $3\times10^5$ cells/flask for 72-hour experiments. Cells were either left untreated or exposed to MSH ($10^{-7}$M) for the times indicated. At 24, 48, and 72 hours, cells were removed, and one portion used to determine tyrosinase activity (panel C) while the other portion of the cells sonicated (3 times 5 seconds each) in sodium phosphate buffer (0.05M, pH 6.8) containing 0.5% Triton X-100 and PMSF (0.1 mM) and prepared for electrophoresis as detailed in Materials and Methods. Following electroblotting, tyrosinase was detected by first incubating the blot in rabbit antityrosinase serum (1/500 dilution in Tris-buffered saline containing 1% milk and 0.05% Tween 20) for 1 hour, followed by washing and incubation in alkaline phosphatase conjugated goat antirabbit immunoglobulin G (IgG) (1/3000) for 1 hour. The immune complexed enzyme was then visualized by incubating the blot in chemiluminescent substrate (Immunlite™, BioRad) for 15 minutes followed by exposure to x-ray film. Panel A shows the autoradiographic image of the blot, and panel B shows the quantitation of the tyrosinase signal by densitometric analysis on a Molecular Dynamics model 300A computing densitometer.)

Figure 4:
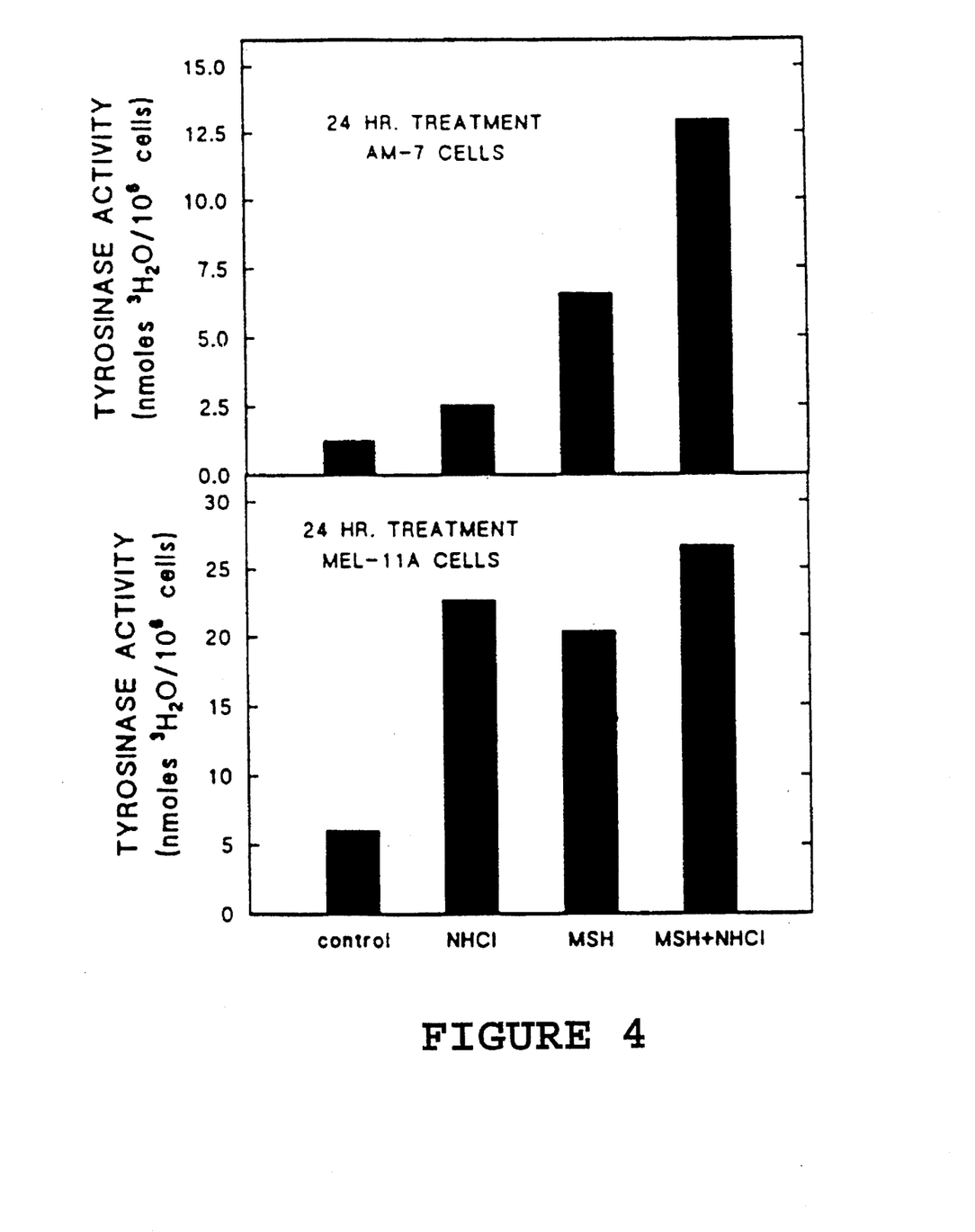
FIG. 4 shows the effects of the lysosomotropic agent ammonium chloride on tyrosinase activity in mouse melanoma cells.

(FIG. 4: Cells were seeded at $2\times10^5$ cell/dish into 60-mm culture dishes and exposed to either ammonium chloride (10 mM), MSH ($10^{-7}$M), or to both compounds for 24 hours in medium containing 1 μCi/ml of [$^3$H]tyrosine. At the end of the incubation, the cells were removed and counted, and the medium assayed for the presence of $^3H_2O$ as described in the text. Values are the averages of quadruplicate dishes.)

The Cloudman S91 murine melanoma cell line, which has been shown to demonstrate a marked increase in tyrosinase activity and melanin synthesis when treated with the peptide hormone MSH (melanocyte-stimulating hormone), represents a good model system for studying the hormonal regulation of pigmentation. The MSH response in these cells can be mimicked by treatment of cells with either cAMP analogues such as dbcAMP (dibutyryl cyclic AMP) or 8-bromo cAMP, or with inhibitors of phosphodiesterase activity such as theophylline and IBMX. Further, MSH activates adenylate cyclase activity, and within minutes of MSH treatment, intracellular cAMP levels rise dramatically. Although it is clear that cAMP is the second messenger for MSH action, tyrosinase activity is not altered by direct incubation with activated protein kinase A, nor is tyrosinase directly phosphorylated by this kinase. Even though cAMP levels rise within minutes of treatment of cells with MSH, no increases in tyrosinase activity are detectable until 6–9 hours after exposure of cells to hormone. This long lag period suggests that a complex cellular pathway must be involved in the hormonal regulation of the enzyme. In an effort to further delineate the cellular pathways involved in the MSH stimulation of tyrosinase activity, we examined the transcriptional and translational requirements for MSH action.

Results from these experiments showed that the hormonal induction of enzyme activity was completely blocked by exposure of cells to either the translational inhibitor cycloheximide or to transcriptional inhibitors such as actinomycin D or α-amanitin. Studies with normal mouse melanocytes either in vitro or in vivo have also demonstrated similar requirements for transcription and translation for MSH action. These findings suggest that MSH regulates tyrosinase activity through enzyme induction, that is, by increasing the synthesis of the enzyme, and evidence has been presented to support this pathway. However, other studies have shown that tyrosinase may be activated in melanoma cells treated with MSH. Discussed herein are studies carried out to examine the contributions of induction and activation to the overall MSH stimulation of tyrosinase activity in melanoma cells. Further, studies on the regulation of tyrosinase in normal human melanocytes are also described and compared to those from melanoma cells.

Studies have suggested that tyrosinase may exist in both catalytically active and inactive states and that hormonal regulation of tyrosinase activity in melanoma cells may proceed, at least in part, through an enzyme activation event. It has been suggested that MSH may promote the activation of inactive tyrosinase by inactivating a tyrosinase inhibitor (presumably through a cAMP-dependent protein kinase-mediated phosphorylation event). Even more elaborate models involving an activation of tyrosinase via internalized MSH receptors have been proposed. Evidence for tyrosinase inhibitors in mouse melanocytes and melanoma has been reported by many investigators, but no such molecules have yet been isolated. It was recently shown that MSH could promote as much as a 7-fold increase in tyrosinase activity in mouse melanoma cells without causing any change in enzyme abundance, a finding that suggests that MSH acts to activate tyrosinase, not increase its synthesis. Other studies have shown that tyrosinase activity is tightly coupled to the abundance of tyrosinase protein, and that the MSH- or IBMX-induced increase in tyrosinase activity correlates with an increase in enzyme abundance. Studies from our laboratory suggested that MSH stimulated tyrosinase activity in mouse melanoma cells by causing both an increase in enzyme abundance and an activation of the enzyme. Since we also found that tyrosinase degradation rates were similar in control and MSH-treated cells, the increased abundance of tyrosinase in MSH-treated cells is likely to an MSH induction of enzyme synthesis. Studies concerned with the effect of MSH on tyrosinase activity in normal mouse follicular melanocytes have also demonstrated that the primary effect of the hormone is to stimulate tyrosinase synthesis and not to activate preexisting enzyme.

In the present study an amelanotic melanoma clone (AM-7) derived from the Cloudman S91 parent cell line was used. These cells have very low basal tyrosinase activities but are highly inducible by MSH. As shown in FIG. 3, an MSH-induced increase in tyrosinase activity and enzyme abundance were tightly correlated. Thus, in these cells, the majority of the response to MSH involves an induction of the enzyme and not a tyrosinase-activation event. As a means of determining what the contribution of enzyme activation might be to the MSH-mediated stimulation of tyrosinase activity, the effect of ammonium chloride and other lysosomotropic agents on preexisting tyrosinase was studied in both the amelanotic melanoma cell clone and in a melanotic clone (MEL-11A), which was also derived from the Cloudman S-91 parent cell line. When the effects of 10-mM ammonium chloride on tyrosinase activity in AM-7 cells were examined, a two-fold increase in enzyme activity (FIG. 4, top) was observed. This stimulation occurred in cells treated with or without cycloheximide (data not shown). In contrast, treatment of these cells with MSH caused a five-fold increase in enzyme activity in 24 hours. Cells treated with both MSH and ammonium chloride showed an approximately ten-fold increase in enzyme activity, a finding that suggests that the two compounds may work through different mechanisms (activation and synthesis) to stimulate tyrosinase activity (FIG. 4, top). For example, although MSH stimulates tyrosinase synthesis, this enzyme may appear at the melanosome in a somewhat catalytically repressed state. The catalytic activity can be increased by two-fold or higher by increasing the pH of the melanosome environment.

The effects of ammonium chloride and MSH in the melanotic melanoma cell clone MEL-11A were examined. It was found that either MSH or ammonium chloride caused a four-fold increase in tyrosinase activity (FIG. 4, bottom). Further, when the two compounds were added together, the stimulation of tyrosinase was not much significantly different than that produced by either one compound alone. Thus, it appears that in this highly pigmented melanoma cell line, MSH likely acts to increase the catalytic activity of preexisting enzyme.

These results suggest that the cellular response to MSH in melanoma cells can vary depending on the level of basal tyrosinase activity. At least for the two cell lines described here, amelanotic clones respond to MSH by increasing enzyme synthesis. In contrast, since tyrosinase transcriptional and translational rates are already high in heavy pigmented cell lines, the action of MSH in these cells seems to be to alter the catalytic activity of existing enzyme. In either cell line, however, preexisting tyrosinase apparently does not exist in its catalytically optimal state.

Figure 5:
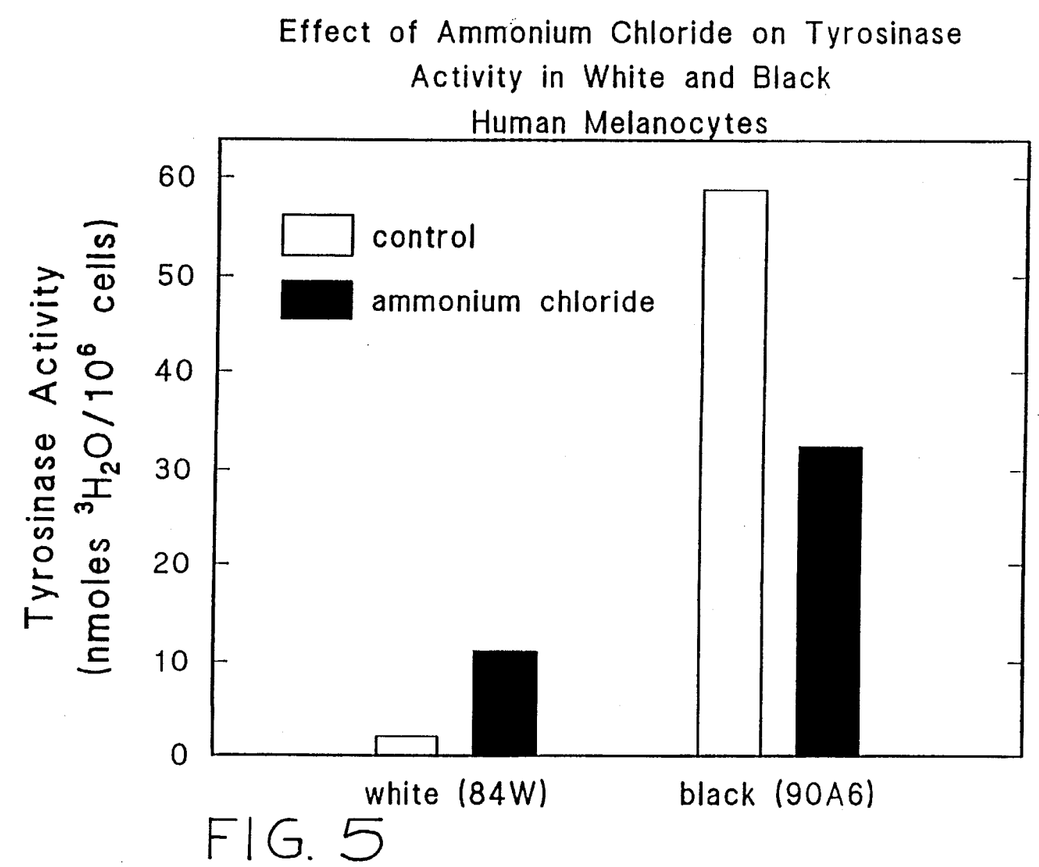
FIG. 5 shows the effects of the lysosomotropic agent ammonium chloride on tyrosinase activity in human melanocytes.
Figure 6:
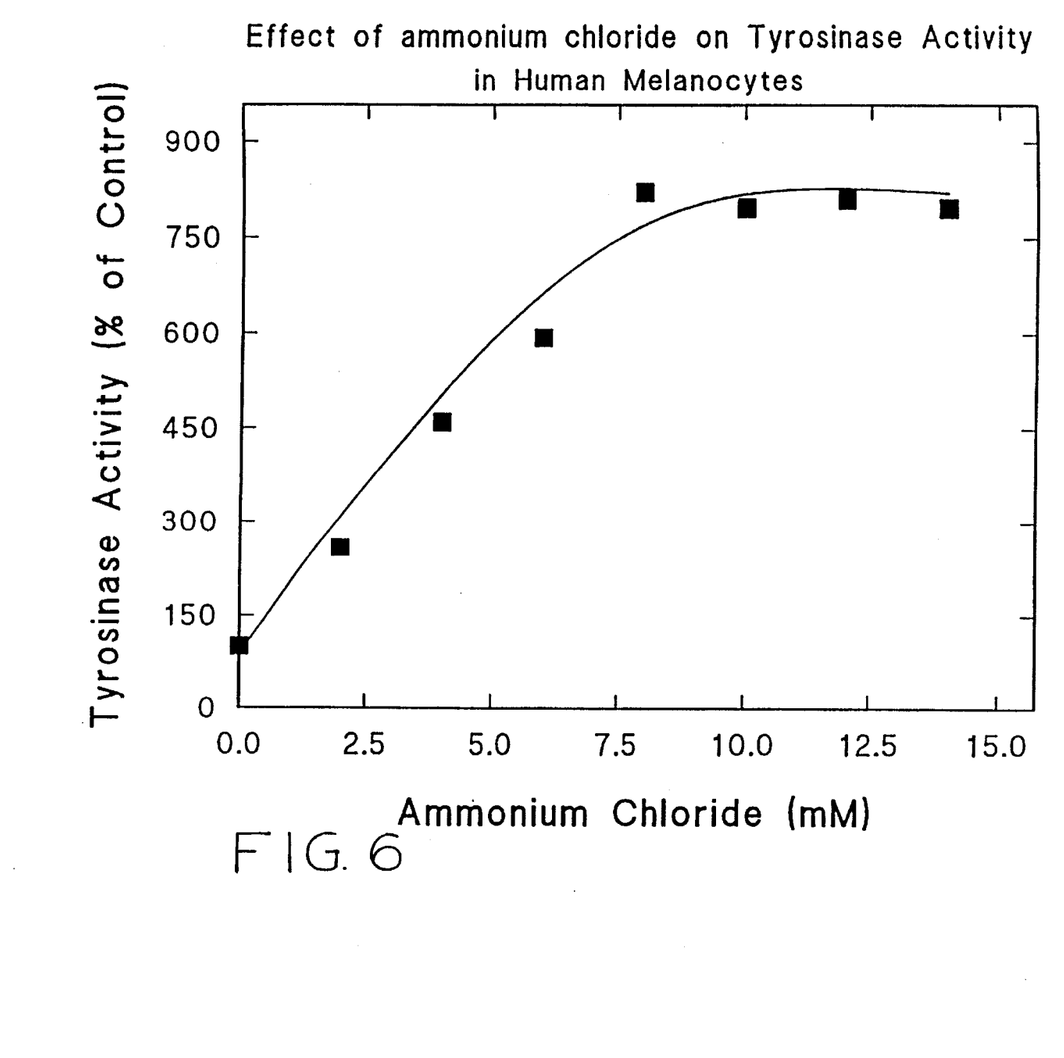
FIG. 6 shows the effects of ammonium chloride on tyrosinase activity in human melanocytes as a percent of the control.
Figure 7:
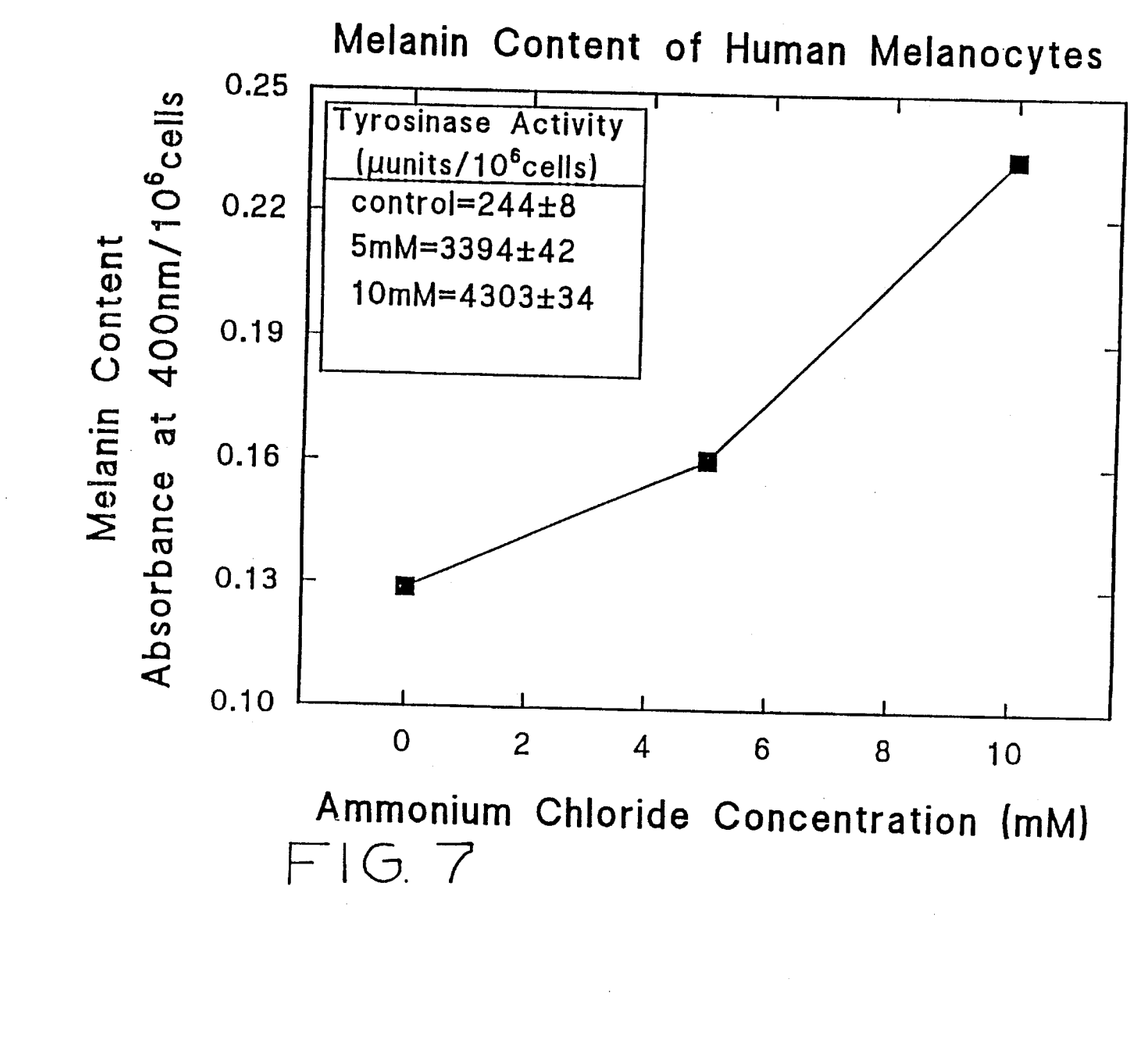
FIG. 7 shows the effects of ammonium chloride on melanin content in human melanocytes.
Figure 8:
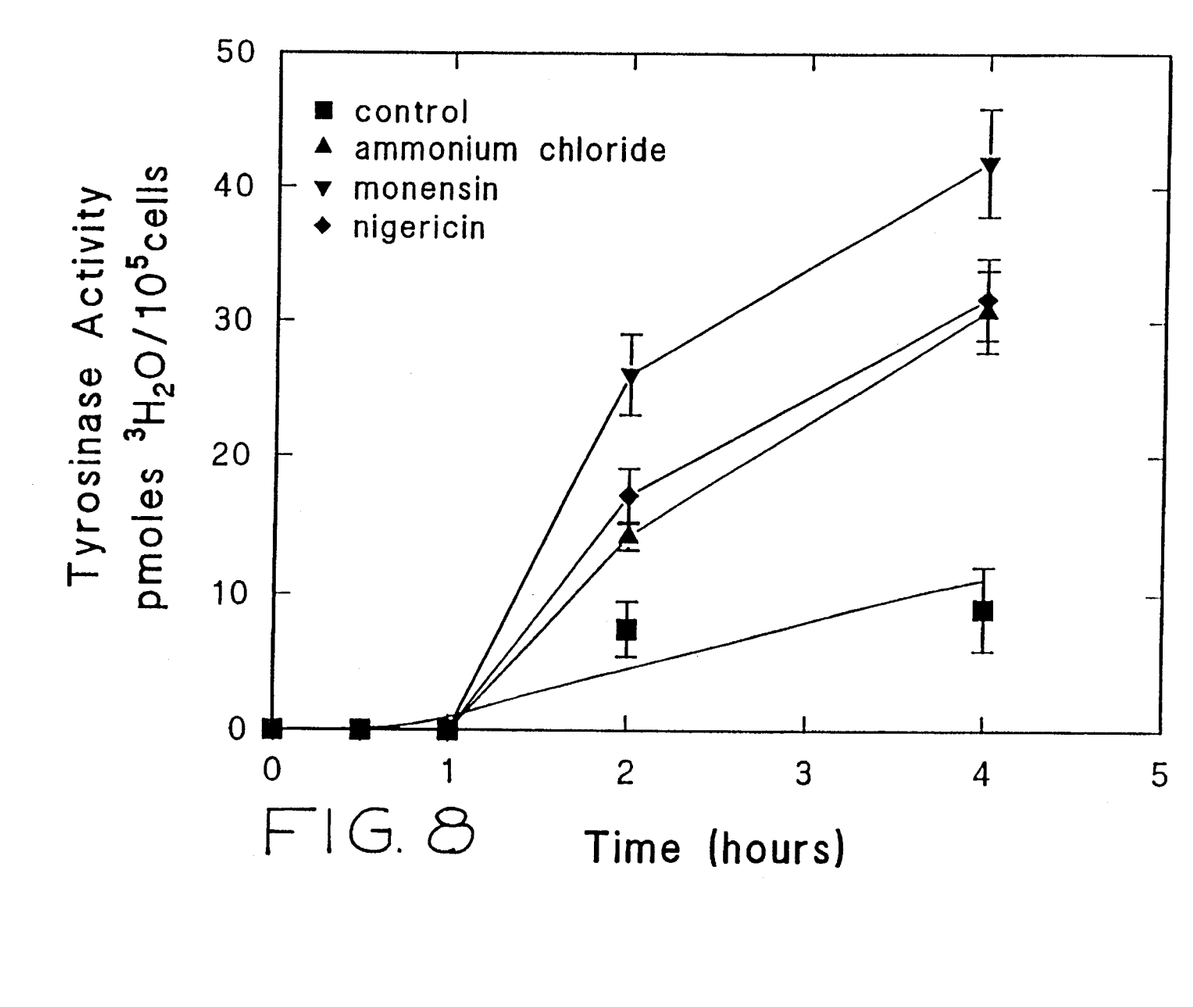
FIG. 8 shows the effects of three lysosomotropic agents on tyrosinase activity.

It has been found that tyrosinase is not as active in white melanocytes as in black melanocytes but appears to be present in equal amounts in black and white skin. As noted above, when human melanocytes were exposed to ammonium chloride, tyrosinase activity in melanocytes from white skin was markedly elevated, while, surprisingly, tyrosinase activity was depressed in melanocytes from black skin (see FIG. 5: Human melanocyte cell cultures were seeded into 50 mm culture dishes and treated with 10 mM ammonium chloride for 48 hours. The activity of tyrosinase, the rate-limiting enzyme for melanin synthesis, was then determined by measuring the amount of tritiated water produced during the conversion of tritiated tyrosine to melanin. As can be seen from the figure, ammonium chloride stimulates tyrosinase in human melanocytes from white-skinned individuals (cell strain #84W) while inhibiting the enzyme in melanocytes from black individuals (cell strain #90A6)). Dose/response parameters for ammonium chloride action were determined. It was found that the stimulatory response was maximal at 7.5 mM (see FIG. 6: Studies were carried out to determine the optimal dose for ammonium chloride stimulation of tyrosinase activity in human melanocytes using cells from cell strain 69W. Human melanocytes from a white individual were seeded into 60 mm dishes and treated with the indicated concentrations of ammonium chloride for 48 hours. Tyrosinase activity was then determined. As can be seen, ammonium chloride maximally stimulates tyrosinase activity at a concentration of 7.5 mM.). Since tyrosinase is the rate-limiting enzyme for melanin synthesis, the stimulation of this enzyme by ammonium chloride should lead to increased melanin content of stimulated cells. As shown in FIG. 7, (studies were carried out to show that, in addition to stimulating tyrosinase activity, ammonium chloride causes an increased accumulation of melanin in human melanocyte cultures. (Referring to FIG. 7, melanocytes cells strain 69W, from a white individual, were treated with various concentrations of ammonium chloride for 3 days. At this time cells were removed from culture dishes, centrifuged, and the cell pellet dissolved in 1M sodium hydroxide at 37° C. for 3 days. The solubilized melanin was measured spectrophotometrically at 400 nm. Cells treated with 10 mM ammonium chloride had twice as much melanin than untreated cells). Ammonium chloride increased tyrosinase activity in melanocytes from white-skinned individuals twenty-fold within 24 hours and by this time melanin contents had increased two-fold. Two other lysosomotropic agents, monensin and nigericin, were tested for their effects on tyrosinase activity. Both stimulated tyrosinase activity (FIG. 8: Cells from cell strain 69W were treated with either ammonium chloride, monensin, or nigericin for up to four hours, and during this incubation period tyrosinase activity was measured at hourly intervals. The figure shows that all of the "lysosomotropic" compounds studied were effective in stimulating tyrosinase activity). Thus, lysosomotropic agents have the ability to stimulate tyrosinase activity and melanin production in human melanocytes derived from white-skinned individuals, and to reduce melanin production in melanocytes from black-skinned people.

The compositions of matter of the present invention additionally comprises an effective amount of a pharmaceutically acceptable topical carrier capable of delivering the agent to the melanocyte under in vivo conditions. The carrier may comprise any solution, suspension, emulsion or any other form which is capable of delivering the agent to the melanocyte under in vivo conditions. "Capable of delivery", as used herein, means that the carrier should permit the agent to cross the stratum corneum and successive cell layers found epidermal to the melanocyte, and/or aids the agent in crossing the melanocyte membrane. Furthermore, the carrier should not substantially interact with the agent so that the agent may perform its function as described herein.

The identity and quantity of the carrier will depend on the identity of the melanin-increasing agent used in the composition of the present invention. However, in many instances, the carrier will represent from about 95 percent to about 99 percent of the composition. In a preferred embodiment, the carrier may comprise 20% water, 50% isopropanol and 30% glycerol, combined with theophylline to produce a composition containing 0.2 percent by weight theophylline. In another embodiment, the carrier may comprise 50% propylene glycol, 20% water and 30% isopropanol to produce a composition containing 0.2 percent by weight theophylline. In another embodiment, the carrier is a vehicle such as a combination of polyethylene glycol, alcohol and water, and may further include an enhancer such as diglycol or oleic acid.

The melanin-increasing agent is present in the compositions of the present invention in any effective amount. An "effective amount" of the melanin-increasing agent is an amount which increases melanogenesis in the treated area of the subject. This amount may vary with, among other things, the identity of melanin-increasing agent and carrier, the subject's skin color and condition, and the degree of tanning and/or photoprotection sought.

This increased melanin would provide a tan without exposure to the sun, and by virtue of its UV absorbing properties, would also provide increased photoprotection from solar radiation. Fair-skinned individuals who tan poorly and are thus at high risk for developing sun-induced skin cancer, would greatly benefit. The increased tan induced by lysosomotropic compounds or other melanogenic compounds will help reduce the risk of skin cancer in these individuals.

In view of the fact that melanin production in epidermal cells from a black-skinned person is decreased when treated with the composition of the present invention, it is contemplated that the composition and method of the present invention would be most effective in increasing epidermal melanin production in persons having skin types 1–4 as defined in the skin color classification system of Pathak as described in the article by M. A. Pathak, "Activation of the Melanocyte System by Ultraviolet Radiation and Cell Transformation", *Annals of the New York Acad. of Sci*, 453:328–339 (1985), which is hereby incorporated by reference herein.

Similarities and Differences in Tyrosinase Regulation in Mouse and Human Melanocytes The successful development of techniques for the propagation of human melanocytes in culture described herein has made it possible to obtain enough melanocytes to begin to characterize the molecular processes that control pigmentation. The results of one study to examine the regulation of tyrosinase in human melanocyte strains derived from different donors suggested that the level of tyrosinase activity in six different cell strains was due predominantly to the abundance of the enzyme in the cell. Thus, highly melanized melanocytes with high tyrosinase activities had more enzyme molecules per cell than did melanocytes with low enzyme activities. Further, melanocytes with low levels of tyrosinase activity synthesized the enzyme at lower rates and degraded it faster than more pigmented cell strains. In another study it was found that some white skin types with low melanin contents and low tyrosinase activities produced as much tyrosinase protein as did more melanized skin types with high enzyme activities. The observation that tyrosinase abundance may be high in melanocytes with low tyrosinase activities suggests that the amount of tyrosinase mRNA in melanocytes with low enzyme activities may also be high. In support of this, it has recently been shown that some amelanotic melanoma cell lines with low or undetectable levels of tyrosinase activity have tyrosinase mRNA levels equivalent to those found in highly pigmented cells. Further, in another study, melanin contents of four human melanomas, two nevus-derived melanocyte strains, and two foreskin-derived melanocyte strains, were not found to correlate with the level of tyrosinase mRNA present in these cells. In addition, a fourfold increase in melanin production in melanocyte cultures treated for three days with IBMX was not accompanied by any increase in the amount of tyrosinase mRNA. Thus, it appears that, at least in some human melanocytes, the regulation of tyrosinase activity is not controlled at the level of tyrosinase gene transcription.

TABLE 4

Comparison of Tyrosinase Activity, Abundance, and Melanin Content in Human Melanocyte Cell strains[a]

| Cell Strain | Tyrosinase Activity (pmoles $^3H_2$)/h per $10^5$ cells) | Relative Abundance[b] (densitometric units) | Melanin Content ($OD_{400}/10^6$ cells) |
|---|---|---|---|
| 69W | 24.7 ± 1.5 | 1345 | 0.034 |
| 84W | 13.8 ± 0.7 | 1151 | 0.009 |
| 89A6 | 237 ± 4.7 | 1781 | 0.686 |
| 93A2 | 46.6 ± 3 | 1962 | 0.025 |

[a]Note: Melanocyte cell strains 69W, 84W, and 93A2 were derived from foreskin of skin type II individuals, while strain 89A6 was obtained from foreskin of a type VI skin type.
[b]Values for tyrosinase abundance are relative volume units calculated from tyrosinase autoradiographic image by a Molecular Dynamics model 300A computing densitometer.

Studies were carried out to compare tyrosinase activities in living cell cultures (in situ assays) with tyrosinase abundance and melanin contents in human melanocyte cell strains derived from different skin types. The results of these studies on four melanocyte cultures are shown in Table 4. It was found that there may be as much as a 17-fold difference in tyrosinase activity and a 76-fold difference in melanin content between a melanocyte strain derived from a white skin type (84W) and one from a highly pigmented individual (skin type VI; 89A6), the difference in tyrosinase abundance between these two cell strains was less than 1.6-fold. Further, one of the white melanocyte strains (93A2), with one-fifth the enzyme activity of the black melanocyte strain, actually had higher amounts of enzyme protein. Next, the amount of tyrosinase mRNA in several melanocyte cell strains were measured and compared to tyrosinase activities. As when tyrosinase abundance was compared to activity, there was a discrepancy between RNA levels and enzyme activity (Table 5). The two melanocyte strains from black skin types (type VI) examined, 41B and 88B, had tyrosinase activities that were 10 times higher than those measured in the two white skin type cell strains (69W and 84W), but tyrosinase mRNA levels among the four cell strains were approximately equal. Thus, although tyrosinase mRNA levels correlate well with the amount of tyrosinase protein present in melanocytes, neither RNA levels nor abundance correlates with enzyme activity. It appears that differences in tyrosinase activity among melanocyte cell strains cannot be explained simply on the basis of differences in tyrosinase mRNA levels or on the number of enzyme molecules per cell. It seems more likely that tyrosinase activity in human melanocytes is regulated, to a great extent, by posttranslational mechanisms.

TABLE 5

Comparison of Tyrosinase Activity and mRNA Levels in Human Melanocytes.

| Cell Strain | Tyrosinase Activity (nmoles $^3H_2O$/h per $10^6$ cells) | Tyrosinase mRNA[a] (relative units) |
|---|---|---|
| 69W (white) | 0.279 ± 0.01 | 3799 |
| 84W (white) | 0.097 ± 0.007 | 5976 |
| 41B (black) | 2.54 ± 0.23 | 5098 |
| 88B (black) | 2.29 ± 0.007 | 4055 |

[a]Values for tyrosinase mRNA are relative volume units calculated from the autoradiograph of northern blots by a Molecular Dynamics model 300A computing densitometer. Blots were reprobed with a GADPH cDNA probe, and tyrosinase mRNA values were normalized to the amount of GAPDH mRNA present.

Hormone responsiveness in human melanocyte cell cultures were examined (for these studies, melanocytes derived from skin type III were used). These results were compared to hormone effects on tyrosinase activity in mouse melanoma cell cultures. Table 6 shows a summary of the results of these experiments. Since mouse melanoma cells respond vigorously to MSH or to compounds that raise intracellular cAMP levels (such as the phosphodiesterase inhibitors, theophylline and IBMX), tyrosinase activities were measured in cells treated with these compounds. Tyrosinase activity and melanin content typically double with a 48-hour exposure to IBMX. MSH, however, produces a smaller (1.5-fold) and somewhat variable increase in tyrosinase activity. The steroid hormones, for the most part, caused little, if any, change in tyrosinase activity at the concentrations used. Ammonium chloride stimulates tyrosinase activity in both mouse melanoma cells and human melanocytes. In light of our findings that human melanocytes derived from white skin types synthesize tyrosinase, which is catalytically less active than in black melanocytes, the results with ammonium chloride suggest that tyrosinase is not irreversibly inactive.

TABLE 6

Tyrosinase Responses in Human Melanocytes and Mouse Melanoma Cells

| Treatment | Effect on Tyrosinase Activity[a] | |
|---|---|---|
| | Human Melanocyte | Mouse Melanoma |
| MSH ($10^{-7}$M) | ± | +++ |
| IBMX ($10^{-4}$M) | + | +++ |
| Theophylline (1 mM) | + | +++ |
| Prostaglandin $E_1$ ($10^{-7}$M) | + | +++ |
| Estradiol ($10^{-7}$M) | Inhibited | No Effect |
| Progesterone ($10^{-7}$M) | ± | ± |
| Triamcinolone acetonide ($10^{-7}$M) | ± | ± |
| Testosterone ($10^{-7}$M) | No effect | No effect |
| Vitamin $D_3$ ($10^{-7}$M) | No effect | No effect |
| TPA ($10^{-7}$M) | No effect | Strongly inhibited |
| Retinoic Acid, all-trans ($10^{-7}$M) | Inhibited | Inhibited[b] |
| Insulin ($10^{-7}$M) | No effect | Strongly inhibited |
| Ammonium chloride (10 mM) | +++[c] | ++ |
| A23187 (calcium ionophore) | No effect | Inhibited |

[a]± = 100–150% of control; + = 150–200%; ++ = >300%.
[b]Retinoic acid at higher concentrations (e.g., $10^{-5}$M) has been shown to stimulate tyrosine activity.
[c]Ammonium chloride only stimulates tyrosinase activity in human melanocytes derived from white skin. Tyrosinase activity in highly melanized melanocytes, derived from black skin types is markedly inhibited by ammonium chloride.

Changes may be made in the construction and the operation of the various components, elements and assemblies described herein or in the steps or the sequence of steps of the methods described herein without departing from the spirit and scope of the invention as defined in the following claims.

What is claimed is:

1. A composition for use in stimulating melanogenesis in human skin cells, comprising:
   an effective amount of a lysosomotropic agent capable of increasing levels of melanin in a human melanocyte; and
   an effective amount of a pharmaceutically acceptable topical carrier capable of delivering the lysosomotropic agent to the melanocyte under in vivo conditions.

2. The composition of claim 1 wherein the lysosomotropic agent is selected from the group consisting of ammonium chloride, monensin and nigericin.

3. The composition of claim 1 in which the lysosomotropic agent comprises from about 0.1 mM to about 100 mM of the composition.

4. The composition of claim 1 in which the lysosomotropic agent comprises from about 0.01 percent to about 10 percent by weight of the composition.

5. The composition of claim 1 in which the lysosomotropic agent comprises from about 0.02 percent to about 5 percent by weight of the composition.

6. The composition of claim 1 in which the lysosomotropic agent comprises from about 0.02 percent to about 2 percent by weight of the composition.

7. The composition of claim 1 further comprising a methylxanthine selected from the group consisting of theophylline, isobutyl methylxanthine, aminophylline and analogs, derivatives, isomers and pharmaceutically acceptable salts of theophylline, isobutyl methylxanthine or aminophylline capable of increasing melanin in the human melanocyte and wherein the pharmaceutically acceptable topical carrier is capable of delivering the methylxanthine to the melanocyte under in vivo conditions.

8. The composition of claim 5 in which the lysosomotropic agent and the methylxanthine each comprise from about 0.01 percent to about 5 percent by weight of the composition.

9. The composition of claim 1 further comprising an effective amount of dibutyryl cAMP.

10. A composition for use in stimulating melanogenesis in human skin cells, comprising:
    an effective amount of a lysosomotropic agent capable of increasing levels of melanin in a human melanocyte;
    an effective amount of a methylxanthine capable of increasing levels of melanin in a human melanocyte; and
    an effective amount of a pharmaceutically acceptable topical carrier capable of delivering the lysosomotropic agent and the methylxanthine to the melanocyte under in vivo conditions.

11. The composition of claim 10 wherein the lysosomotropic agent is selected from the group consisting of ammonium chloride, monensin and nigericin.

12. The composition of claim 10 in which the lysosomotropic agent comprises from about 0.1 mM to about 100 mM of the composition.

13. The composition of claim 10 in which the lysosomotropic agent comprises from about 0.01 percent to about 10 percent by weight of the composition.

14. The composition of claim 10 in which the lysosomotropic agent comprises from about 0.02 percent to about 5 percent by weight of the composition.

15. The composition of claim 10 in which the lysosomotropic agent comprises from about 0.02 percent to about 2 percent by weight of the composition.

16. The composition of claim 10 wherein the methylxanthine is selected from the group consisting of theophylline, isobutyl methylxanthine, aminophylline and analogs, derivatives, isomers and pharmaceutically acceptable salts of theophylline, isobutyl methylxanthine or aminophylline capable of increasing melanin in the human melanocyte and wherein the pharmaceutically acceptable topical carrier is capable of delivering the methylxanthine to the melanocyte under in vivo conditions.

17. The composition of claim 10 in which the lysosomotropic agent and the methylxanthine together comprise from about 0.01 percent to about 10 percent by weight of the composition.

18. The composition of claim 10 further comprising an effective amount of dibutyryl cAMP.

19. A method for stimulating melanogenesis in human skin cells, comprising:
    providing a composition comprising:
    an effective amount of a lysosomotropic agent capable of increasing levels of melanin in a human melanocyte, and
    an effective amount of a pharmaceutically acceptable topical carrier capable of delivering the lysosomotropic agent to the melanocyte under in vivo conditions; and
    applying the composition topically to human skin.

20. The method of claim 19 wherein in the step of providing the composition the lysosomotropic agent is selected from the group consisting of ammonium chloride, monensin and nigericin.

21. The method of claim 19 wherein in the step of providing the composition, the lysosomotropic agent comprises from about 0.1 mM to about 100 mM of the composition.

22. The method of claim 19 wherein in the step of providing the composition, the lysosomotropic agent comprises from about 0.01 percent to about 10 percent by weight of the composition.

23. The method of claim 19 wherein in the step of providing the composition, the lysosomotropic agent comprises from about 0.02 percent to about 5 percent by weight of the composition.

24. The method of claim 19 wherein in the step of providing the composition, the lysosomotropic agent comprises from about 0.02 percent to about 2 percent by weight of the composition.

25. The method of claim 19 wherein in the step of providing the composition, the composition further comprises a methylxanthine selected from the group consisting of theophylline, isobutyl methylxanthine, aminophylline and analogs, derivatives, isomers and pharmaceutically acceptable salts of theophylline, isobutyl methylxanthine or aminophylline capable of increasing melanin in the human melanocyte and wherein the pharmaceutically acceptable topical carrier is capable of delivering the methylxanthine to the melanocyte under in vivo conditions.

26. The method of claim 25 wherein in the step of providing the composition, the lysosomotropic agent and the methylxanthine together comprise from about 0.01 percent to about 10 percent by weight of the composition.

27. The method of claim 19 wherein in the step of providing the composition, the composition further comprises an effective amount of dibutyryl cAMP.

* * * * *

UNITED STATES PATENT AND TRADEMARK OFFICE
CERTIFICATE OF CORRECTION

PATENT NO. : 5,554,359
DATED : September 10, 1996
INVENTOR(S) : Fuller

It is certified that error appears in the above-indentified patent and that said Letters Patent is hereby corrected as shown below:

Cover page, Related U.S. Application Data, second line, please delete "abandoned".

Column 8, line 56, please delete "average" and substitute therefor --averages--.

Column 10, line 21, please delete "neonares" and substitute therefor --neonates--.

Column 13, line 40, please delete "50" and substitute therefor --60--.

Signed and Sealed this

Fourteenth Day of January, 1997

Attest:

BRUCE LEHMAN

Attesting Officer   Commissioner of Patents and Trademarks